United States Patent
Qu et al.

(10) Patent No.: US 9,528,126 B2
(45) Date of Patent: *Dec. 27, 2016

(54) METHODS FOR PRODUCING PREPARATIONS OF RECOMBINANT AAV VIRIONS SUBSTANTIALLY FREE OF EMPTY CAPSIDS

(75) Inventors: Guang Qu, Alameda, CA (US); John Fraser Wright, Mill Valley, CA (US)

(73) Assignee: Genzyme Corporation, Cambridge, MA (US)

( * ) Notice: Subject to any disclaimer, the term of this patent is extended or adjusted under 35 U.S.C. 154(b) by 319 days.

This patent is subject to a terminal disclaimer.

(21) Appl. No.: 13/368,167

(22) Filed: Feb. 7, 2012

(65) Prior Publication Data

US 2012/0135515 A1 May 31, 2012

Related U.S. Application Data

(60) Continuation of application No. 11/809,655, filed on Jun. 1, 2007, which is a division of application No. 10/851,688, filed on May 21, 2004.

(60) Provisional application No. 60/472,384, filed on May 21, 2003, provisional application No. 60/549,756, filed on Mar. 2, 2004.

(51) Int. Cl.
| | | |
|---|---|---|
| C12N 7/02 | (2006.01) | |
| C12N 15/86 | (2006.01) | |
| C12N 7/00 | (2006.01) | |
| C12N 15/82 | (2006.01) | |

(52) U.S. Cl.
CPC ............... *C12N 15/86* (2013.01); *C12N 7/00* (2013.01); *C12N 2750/14143* (2013.01); *C12N 2750/14151* (2013.01)

(58) Field of Classification Search
CPC . C12N 15/86; C12N 7/00; C12N 2750/14151; C12N 15/8645; C12N 2750/14051; C07K 14/005; C07K 2319/00; C07K 14/47; C07K 14/55; C07K 14/715; C07K 2319/715; C07K 14/39; C07K 14/395; C07K 14/4702; C07K 14/4705; C07K 14/7051; C07K 14/70578; C07K 2319/003; C07K 2319/09; C07K 1/18; A61K 48/0091; A61K 39/23; A61K 38/1841
See application file for complete search history.

(56) References Cited

U.S. PATENT DOCUMENTS

| | | | |
|---|---|---|---|
| 6,566,118 B1 | 5/2003 | Atkinson et al. | |
| 6,593,123 B1 | 7/2003 | Wright et al. | |
| 6,989,264 B2 | 1/2006 | Atkinson et al. | |
| 6,995,006 B2* | 2/2006 | Atkinson et al. | ............. 435/239 |
| 7,261,544 B2* | 8/2007 | Qu et al. | ............. 425/239 |
| 2002/0037565 A1 | 3/2002 | Blanche et al. | |
| 2004/0110266 A1 | 6/2004 | Chiorini et al. | |

FOREIGN PATENT DOCUMENTS

| | | |
|---|---|---|
| WO | WO 97/08298 A1 | 3/1997 |
| WO | WO 99/11764 A2 | 3/1999 |
| WO | WO 02/12455 A1 | 2/2002 |
| WO | WO 03/046142 A | 6/2003 |
| WO | WO2004/113494 A2 | 12/2004 |

OTHER PUBLICATIONS

Gao et al. Human Gene Therapy 2000, vol. 11, pp. 2079-2091.*
Anderson, et al., "A Method for the Preparation of Highly Purified Adeno-Associated Virus Using Affinity Column Chromatography, Protease Digestion, and Solvent Extraction," *Journal of Viralogical Methods* 85:23-34 (2000).
Brument, et al., "A Versitile and Scalable Two-Step Ion-Exchange Chromatography Process for the Purification of Recombinant Adeno-Associated Virus Serotype-2 and -5," *Molecular Therapy* 6(5):678-686 (2002).
Clark, et al., "Highly Purified Recombinant Adeno-Associated Virus Vectors Are Biologically Active and Free of Detectable Helper and Wild-Type Viruses," *Human Gene Therapy* 10:1031-1039 (1999).
Davidoff, et al., "Purification of Recombinant Adeno_Associated Virus Type 8 Vectors by Ion Exchange Chromatography Generates Clinical Grade Vector Stock," *Journal of Virilogical Methods* 121:209-215 (2004).
Debelak, et al., "Cation-Exchange High-Performance Liquid Chromatography of Recombinant Adeno-Associated Virus Type-2," *J Chromat B* 740:195-202 (2000).
Feit et al., J. Pat. Trade. Off. Soc., 85(1):5-21 (2003).
Gao, et al., "Purification of Recombinant Adeno-Associated Virus Vectors by Column Chromatography and It's Performance In Vivo," *Human Gene Therapy* 11:2079-2091 (2000).
Grimm, et al., "Titration of AAV-2 Particles Via a Novel Capsid ELISA: Packaging of Genomes Can Limit Production of Recombinant AAV-2," *Gene Therapy* 6:1322-1330 (1999).
Kaludov, et al., "Scalable Purification of Adeno-Associated Virus Type 2,4, or 5 Using Ion-Exchange Chromatography," *Human Gene Therapy* 13:1235-1243 (2002).
Lewis, et al., "Kinetic Study of the Deamidation of Growth Hormone and Prolatin," *Biochimica et Biophysica Acta* 214:498-508 (1970).
Parker, et al., "In Vivo Performance of AAV-2 Vectors Purified by CsCI Gradient Centrifugation or column Chromatography," *Molecular Therapy* 7:S390 (2003).

(Continued)

*Primary Examiner* — Bao Li
(74) *Attorney, Agent, or Firm* — Roberta L. Robins; Robins Law Group

(57) ABSTRACT

Methods for separating AAV empty capsids from mixtures of AAV vector particles and AAV empty capsids are described. The methods use column chromatography techniques and provide for commercially viable levels of recombinant AAV virions.

11 Claims, 5 Drawing Sheets

(56) References Cited

OTHER PUBLICATIONS

Potter, et al., "Streamlined Large-Scale Production of Recombinant Adeno-Associated Virus (rAAV) Vectors," *Methods in Enzymology* 346:413-430 (2002).

Qu, et al., Characterization of AAV Vectors Expressing Human Coagulation Factor IX Produced At Intermediate Scale, *Molecular Therapy* 5:S50 (2002).

Qu, et al., "Scaling-Up Production of Recombinant AAV Vectors for Clinical Applications," *Current Opinion in Drug Discovery & Development* 3(6):750-755 (2000).

Qu, et al., "Development of a Scalable column Chromatography-Based Purification Process to Manufacture Empty Capsid-Free AAV Vectors," *Mol Ther* 9:S162 Abst.# 424 (2004).

Snyder, et al., "Production of Clinical-Grade Recombinant Adeno-Associated Virus Vectors," *Current Opinion in Biotechnology* 13:418-423 (2002).

Sommer, et al., "Quantification of Adeno-Associated Virus Particles and Empty Capsids by Optical Density Measuremnt," *Molecular Therapy* 7:122-128 (2003).

Summerford, et al., Membrane-Associated Heperan Sulfate Proteoglycan Is a Receptor for Adeno-Associated Viruse Type 2 Virions, *Journal of Virology* 72:1438-1445 (1998).

Timpe et al., Current Gene Therapy 5:273-284 (2005).

Vellekamp, et al., "Empty Capsids in Column-Purified Recombinant Adenovirus Preparations," *Human Gene Therapy* 12:1923-1936 (2001).

Wright, et al., "Identification of Factors That Contribute to Recombinant AAV2 Particle Aggregation and Methods to Prevent Its Occurance During Vector Purification and Formulation," *Molecular Therapy*12:171-178 (2005).

Wu, et al., "A Novel Method for Purification of Recombinant Adeno-Associated Virus Vectors on a Large Scale," Chinese Science Bulletine 46:485-489 (2001).

Zoluthkin, et al., "Recombinant Adeno-Addociated Virus Purification Using Novel Methods Improves Infectious Titer and Yield," *Gene Therapy* 6:973-985 (1999).

US Priority Document 1—U.S. Appl. No. 60/472,384, filed May 2003 original file name: D2—Priority Document 2003—U.S. Pat. No. 472384.

US Priority Document 2—U.S. Appl. No. 60/549,756, filed Mar. 2004 original file name: D3—Priority Document 2004—U.S. Pat. No. 549756.

Response from the Applicant in the US proceedings on Apr. 2011 original file name: D13—U.S. Pat. No. 8137948—Response from Applicant.

Burova et al., Chromatographic Purification of Recombinant Adenoviral and Adeno-Associated Viral Vectors: Methods and Implications, Gene Therapy, vol. 12, S5-S17, 2005.

Drittanti et al., Optimised Helper Virus-Free Production of High-Quality Adeno-Associated Virus Vectors, The Journal of Gene Medicine, vol. 3, pp. 59-71 (2001).

Qu et al., Separation of Adeno-Associated Virus Type 2 Empty Particles from Genome Containing Vectors by Anion-Exchange Column Chromatography, Journal of Virological Methods, vol. 140, pp. 183-192 (2007).

Smith et al., Serum-Free Production and column Purification of Adeno-Associated Virus Type 5, Journal of Virological Methods, vol. 114, pp. 115-124 (2003).

Urabe et al., Removal of Empty Capsids from Type 1 Adeno-Associated Virus Vector Stocks by Anion-Exchange Chromatography Potentiates Transgene Expression, Molecular Therapy, vol. 13, No. 4, pp. 823-828.

Wright et al., Product-Related Impurities in Clinical-Grade Recombinant AAV Vectors: Characterization and Risk Assessment, Biomedicines, vol. 2, pp. 80-97 (2014).

Notice of Opposition to a European patent, patent No. EP2277996 dated Jun. 3, 2015.

\* cited by examiner

| Samples | Capsids/ml | Vgs/ml | Ratio of capsid/vg |
|---|---|---|---|
| Starting Materials** | 1.07E+13 | 6.47E+11 | 16.56 |
| Fraction 25*** | 9.59E+10 | 1.05E+11 | 0.92 |

*FIG. 2*

METHODS FOR PRODUCING PREPARATIONS OF RECOMBINANT AAV VIRIONS SUBSTANTIALLY FREE OF EMPTY CAPSIDS

CROSS-REFERENCE TO RELATED APPLICATIONS

This application is a continuation of U.S. application Ser. No. 11/809,655, filed Jun. 1, 2007, which is a divisional of U.S. application Ser. No. 10/851,688, filed May 21, 2004, now U.S. Pat. No. 7,261,544, from which applications priority is claimed pursuant to 35 U.S.C. §120, and claims the benefit under 35 U.S.C. §119(e)(1) to U.S. Provisional Application Nos. 60/472,384, filed May 21, 2003 and 60/549,756, filed Mar. 2, 2004, all of which applications are hereby incorporated by reference in their entireties.

TECHNICAL FIELD

The invention relates to methods for purifying adeno-associated virus (AAV) virions. More particularly, the invention relates to methods for purifying recombinant AAV (rAAV) virions containing packaged genomes from mixtures of AAV virions containing both packaged rAAV virions and AAV empty capsids lacking said genomes.

BACKGROUND

Gene therapy methods are currently being developed that safely and persistently deliver therapeutically effective quantities of gene products to patients. Using these methods, a nucleic acid molecule can be introduced directly into a patient (in vivo gene therapy), or into cells isolated from a patient or a donor, which are then subsequently returned to the patient (ex vivo gene therapy). The introduced nucleic acid then directs the patient's own cells or grafted cells to produce the desired therapeutic product. Gene therapy also allows clinicians to select specific organs or cellular targets (e.g., muscle, blood cells, brain cells, etc.) for therapy.

Nucleic acids may be introduced into a patient's cells in several ways, including viral-mediated gene delivery, naked DNA delivery, and transfection methods. Viral-mediated gene delivery has been used in a majority of gene therapy trials. C. P. Hodgson *Biotechnology* (1995) 13:222-225. The recombinant viruses most commonly used are based on retrovirus, adenovirus, herpesvirus, pox virus, and adeno-associated virus (AAV).

Recombinant adeno-associated viral vectors hold promise as gene delivery vectors for human gene therapy. However, one significant obstacle to using such vectors as drugs is the development of a truly scaleable process to produce and purify the vector at commercially viable levels. For a review of the challenges involved in scaling AAV vector production for commercial use, see Qu and Wright, *Cur. Opin. Drug Disc. and Develop.* (2000) 3:750-755. Recently, several potentially scalable column chromatography techniques to purify rAAV virions have been developed. While these column chromatography-based purification methods have demonstrated that rAAV virions can be purified at large scale, the preparation of purified virions using column chromatography contains a significant amount of AAV empty capsids. The typical ratio of empty capsids to virions containing a heterologus gene of interest ("AAV vector particles") is about 10 or higher, i.e., approximately 90% of the recovered vectors are empty capsids.

The presence of a large amount of empty capsids may hinder clinical applications, e.g., by eliciting unwanted immune responses to the capsid protein or by competing for target cell surface binding sites. Consequently, techniques have been developed to remove the empty capsids from rAAV virion preparations. These techniques typically rely on ultracentrifugation, for example gradient centrifugation in cesium chloride or iodixanol. Such centrifugation techniques are labor intensive, typically result in low vector yield, and are not scalable. Kaludov et al., (2002) *Hum. Gene Ther.* 13:1235-1243, describe methods of purifying rAAV-2, -4 and -5 vectors using anion exchange columns. However, the experimenters were only able to recover 2%, 0.6% and 6.3%, respectively, as packaged genomes, even after pooling the eluates and concentrating the fractions.

Thus, there remains a need for new ways of eliminating or reducing the numbers of empty capsids from stocks of AAV vector particles so that manufacturing capability is enhanced.

SUMMARY OF THE INVENTION

The present invention is based on the discovery of efficient and commercially viable methods for preparing stocks of rAAV virions with reduced amounts of empty capsids. The inventors herein have found that empty capsids can be separated from rAAV virions containing genetic material ("AAV vector particles") using column chromatography techniques. This result is surprising as it was previously believed that empty and packaged capsids had identical surface properties. To the best of the inventors' knowledge, this is the first demonstration that viral particle charge and/or the charge-density are different between empty particles and full particles. The techniques described herein provide efficient and scalable methods to separate AAV empty capsids from AAV vector particles.

Accordingly, in one embodiment, the invention is directed to a method for purifying AAV vector particles from an AAV preparation comprising AAV vector particles and AAV empty capsids, to provide an AAV product substantially free of AAV empty capsids. The method comprises:

(a) providing a host cell comprising AAV vector particles;

(b) lysing the host cell to obtain a crude cell lysate comprising AAV vector particles and AAV empty capsids;

(c) applying the crude cell lysate to a first cation exchange chromatograhphy column under conditions whereby the AAV vector particles and the AAV empty capsids bind the column;

(d) eluting the AAV vector particles and the AAV empty capsids under non-separating conditions to provide an AAV preparation comprising AAV vector particles and AAV empty capsids;

(e) applying the AAV preparation from (d) to a second cation exchange chromatography column under conditions whereby the AAV vector particles and the AAV empty capsids bind the column;

(f) adding a low salt buffer to the column from (e) under conditions whereby AAV vector particles are eluted and AAV empty capsids remain bound to the column; and (g) collecting eluted fractions from (f) that comprise AAV vector particles to provide an AAV product substantially free of AAV empty capsids.

In additional embodiments, the above method further comprises:

(h) applying the fractions from step (g) to an anion exchange chromatography column under conditions whereby the AAV vector particles and AAV empty capsids, if present, bind the column;

(i) adding a low salt buffer to the column from (h) under conditions whereby AAV empty capsids are eluted and AAV vector particles remain bound to the column;

(j) adding a high salt buffer to the column from (i) under conditions whereby AAV vector particles are eluted;

(k) collecting fractions from (j) that comprise AAV vector particles to provide an AAV product substantially free of AAV empty capsids.

In yet a further embodiment, the invention is directed to a method for purifying AAV vector particles from an AAV preparation comprising AAV vector particles and AAV empty capsids, to provide an AAV product substantially free of AAV empty capsids. The method comprises:

(a) providing a host cell comprising AAV vector particles;

(b) lysing the host cell to obtain a crude cell lysate comprising AAV vector particles and AAV empty capsids;

(c) clarifying the crude cell lysate to provide a clarified cell lysate;

(d) applying the clarified cell lysate to a first cation exchange chromatograhphy column comprising a matrix with the functional ligand $R\text{---}SO_3\text{---}$, under conditions whereby the AAV vector particles and the AAV empty capsids bind the column;

(e) eluting the AAV vector particles and the AAV empty capsids under non-separating conditions to provide an AAV preparation comprising AAV vector particles and AAV empty capsids;

(f) applying the AAV preparation from (e) to a second cation exchange chromatography column under conditions whereby the AAV vector particles and the AAV empty capsids bind the column;

(g) adding a low salt buffer to the column from (f) under conditions whereby AAV vector particles are eluted and AAV empty capsids remain bound to the column;

(h) collecting eluted fractions from (g) that comprise AAV vector particles;

(i) applying the fractions from step (h) to an anion exchange chromatography column under conditions whereby said AAV vector particles and AAV empty capsids, if present, bind the column;

(j) adding a low salt buffer to the column from (i) under conditions whereby AAV empty capsids are eluted and AAV vector particles remain bound to the column;

(k) adding a high salt buffer to the column from (j) under conditions whereby AAV vector particles are eluted; and (l) collecting eluted fractions from (k) that comprise AAV vector particles to provide an AAV product substantially free of AAV empty capsids.

In another embodiment, the invention is directed to a method for purifying AAV vector particles from an AAV preparation comprising AAV vector particles and AAV empty capsids, to provide an AAV product substantially free of AAV empty capsids. The method comprises:

(a) providing a host cell comprising AAV vector particles;

(b) lysing the host cell to obtain a crude cell lysate comprising AAV vector particles and AAV empty capsids;

(c) applying the crude cell lysate to a cation exchange chromatograhphy column under conditions whereby the AAV vector particles and the AAV empty capsids bind the column;

(d) eluting the AAV vector particles and the AAV empty capsids under non-separating conditions to provide an AAV preparation comprising AAV vector particles and AAV empty capsids;

(e) applying the AAV preparation from (d) to an anion exchange chromatography column under conditions whereby the AAV vector particles and the AAV empty capsids bind the column;

(f) adding a low salt buffer to the column from (e) under conditions whereby AAV empty capsids are eluted and AAV vector particles remain bound to the column;

(g) adding a high salt buffer to the column from (f) under conditions whereby AAV vector particles are eluted;

(h) collecting eluted fractions from (g) that comprise AAV vector particles to provide an AAV product substantially free of AAV empty capsids.

In additional embodiments, the above method further comprises:

(i) applying the AAV preparation from (h) to a second anion exchange chromatography column under conditions whereby the AAV vector particles and the AAV empty capsids, if present, bind the column;

(j) adding a low salt buffer to the column from (i) under conditions whereby AAV empty capsids are eluted and AAV vector particles remain bound to the column;

(k) adding a high salt buffer to the column from (j) under conditions whereby AAV vector particles are eluted;

(l) collecting eluted fractions from (k) that comprise AAV vector particles to provide an AAV product substantially free of AAV empty capsids.

In alternative embodiments, the method further comprises:

(i) applying the AAV preparation from (h) to a second cation exchange chromatography column under conditions whereby the AAV vector particles and the AAV empty capsids bind the column;

(j) adding a low salt buffer to the column from (i) under conditions whereby AAV vector particles are eluted and AAV empty capsids remain bound to the column; and (k) collecting eluted fractions from (j) that comprise AAV vector particles to provide an AAV product substantially free of AAV empty capsids.

In certain embodiments of all of the above methods, the first cation exchange column and/or the second cation exchange column comprises a carboxymethylated or sulfonated matrix, such as a matrix that comprises the functional ligand $R\text{---}SO_3\text{---}$.

In additional embodiments of all of the above methods, the AAV vector particles are present in the AAV product in an amount of at least 50%, such as in an amount of at least 75%, e.g. in an amount of at least 85%, or at least 90%.

In yet further embodiments of all of the above methods, the AAV vector particles are derived from AAV-2 or AAV-5.

These and other embodiments of the subject invention will readily occur to those of skill in the art in view of the disclosure herein.

BRIEF DESCRIPTION OF THE FIGURES

In FIG. 1A, the resins tested were as follows: Lane 1: control; Lanes 2 and 3: MACRO PREP Q (strong anion-exchanger available from BioRad, Hercules, Calif.); Lanes 4 and 5: UNOSPHERE Q (strong anion-exchanger available from BioRad, Hercules, Calif.); Lanes 6 and 7: POROS 50HQ (strong anion-exchanger available from Applied Biosystems, Foster City, Calif.); Lanes 8 and 9: POROS 50D (weak anion-exchanger available from Applied Biosystems, Foster City, Calif.). In FIG. 1B, the resins tested were as follows: Lane 1: control; Lanes 2 and 3: POROS 50PI (weak anion-exchanger available from Applied Biosystems, Foster City, Calif.); Lanes 4 and 5: SOURCE 30Q (strong anion-exchanger available from Amersham Biosciences, Piscataway, N.J.); Lanes 6 and 7: DEAE SEPHAROSE (weak anion-exchanger available from Amersham Biosciences, Piscataway, N.J.); Lanes 8 and 9: Q SEPHAROSE (strong anion-exchanger available from Amersham Biosciences, Piscataway, N.J.). For both FIGS. 1A and 1B, Lanes 2, 4, 6 and 8 used a low salt (50 mM NaCl) washing fraction; Lanes 3, 5, 7 and 9 used a high salt (1M NaCl) washing fraction.

FIG. 2 shows an analysis of AAV empty capsids and AAV vector particles (Vgs) before and after separation using anion exchange chromatography as described in the examples.

DETAILED DESCRIPTION OF THE INVENTION

Figure 1:
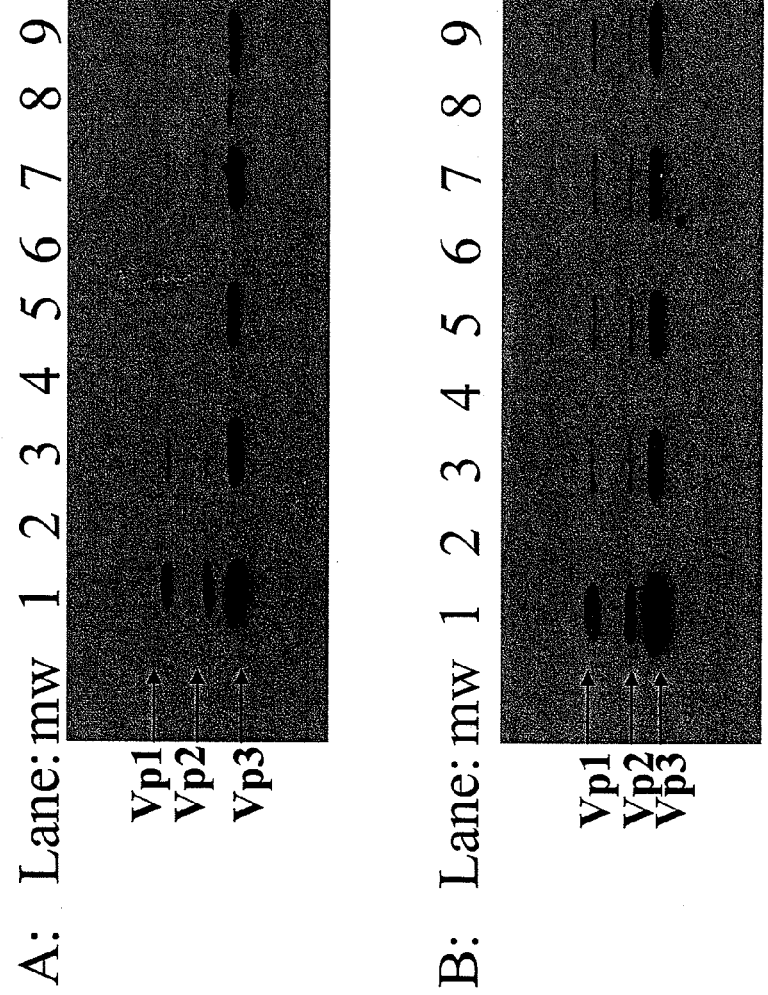
FIGS. 1A and 1B show the binding characteristics of a crude lysate containing both AAV vector particles and AAV empty capsids.

The practice of the present invention will employ, unless otherwise indicated, conventional methods of virology, microbiology, molecular biology and recombinant DNA techniques within the skill of the art. Such techniques are explained fully in the literature. See, e.g., Sambrook et al. *Molecular Cloning: A Laboratory Manual* (Current Edition); *DNA Cloning: A Practical Approach*, Vol. I & II (D. Glover, ed.); *Oligonucleotide Synthesis* (N. Gait, ed., Current Edition); *Nucleic Acid Hybridization* (B. Hames & S. Higgins, eds., Current Edition); *Transcription and Translation* (B. Hames & S. Higgins, eds., Current Edition); *CRC Handbook of Parvoviruses*, vol. I & II (P. Tijssen, ed.); *Fundamental Virology*, 2nd Edition, vol. I & II (B. N. Fields and D. M. Knipe, eds.); Freshney *Culture of Animal Cells, A Manual of Basic Technique* (Wiley-Liss, Third Edition); and Ausubel et al. (1991) *Current Protocols in Molecular Biology* (Wiley Interscience, NY).

All publications, patents and patent applications cited herein, whether supra or infra, are hereby incorporated by reference in their entirety.

1. DEFINITIONS

In describing the present invention, the following terms will be employed, and are intended to be defined as indicated below.

It must be noted that, as used in this specification and the appended claims, the singular forms "a", "an" and "the" include plural referents unless the content clearly dictates otherwise. Thus, for example, reference to "a packaged capsid" includes a mixture of two or more such capsids, and the like.

By "vector" is meant any genetic element, such as a plasmid, phage, transposon, cosmid, chromosome, virus, virion, etc., which is capable of replication when associated with the proper control elements and which can transfer gene sequences between cells. Thus, the term includes cloning and expression vehicles, as well as viral vectors.

By an "AAV vector" is meant a vector derived from an adeno-associated virus serotype, including without limitation, AAV-1, AAV-2, AAV-3, AAV-4, AAV-5, AAV-6, AAV-7 and AAV-8. AAV vectors can have one or more of the AAV wild-type genes deleted in whole or part, preferably the rep and/or cap genes, but retain functional flanking ITR sequences. Functional ITR sequences are necessary for the rescue, replication and packaging of the AAV virion. Thus, an AAV vector is defined herein to include at least those sequences required in cis for replication and packaging (e.g., functional ITRs) of the virus. The ITRs need not be the wild-type nucleotide sequences, and may be altered, e.g., by the insertion, deletion or substitution of nucleotides, so long as the sequences provide for functional rescue, replication and packaging.

"AAV helper functions" refer to AAV-derived coding sequences which can be expressed to provide AAV gene products that, in turn, function in trans for productive AAV replication. Thus, AAV helper functions include both of the major AAV open reading frames (ORFs), rep and cap. The Rep expression products have been shown to possess many functions, including, among others: recognition, binding and nicking of the AAV origin of DNA replication; DNA helicase activity; and modulation of transcription from AAV (or other heterologous) promoters. The Cap expression products supply necessary packaging functions. AAV helper functions are used herein to complement AAV functions in trans that are missing from AAV vectors.

The term "AAV helper construct" refers generally to a nucleic acid molecule that includes nucleotide sequences providing AAV functions deleted from an AAV vector which is to be used to produce a transducing vector for delivery of a nucleotide sequence of interest. AAV helper constructs are commonly used to provide transient expression of AAV rep and/or cap genes to complement missing AAV functions that are necessary for AAV replication; however, helper constructs lack AAV ITRs and can neither replicate nor package themselves. AAV helper constructs can be in the form of a plasmid, phage, transposon, cosmid, virus, or virion. A number of AAV helper constructs have been described, such as the commonly used plasmids pAAV/Ad and pIM29+45 which encode both Rep and Cap expression products. See, e.g., Samulski et al. (1989) *J. Virol.* 63:3822-3828; and McCarty et al. (1991) *J. Virol.* 65:2936-2945. A number of other vectors have been described which encode Rep and/or Cap expression products. See, e.g., U.S. Pat. Nos. 5,139,941 and 6,376,237.

The term "accessory functions" refers to non-AAV derived viral and/or cellular functions upon which AAV is dependent for its replication. Thus, the term captures proteins and RNAs that are required in AAV replication, including those moieties involved in activation of AAV gene transcription, stage specific AAV mRNA splicing, AAV DNA replication, synthesis of Cap expression products and AAV capsid assembly. Viral-based accessory functions can be derived from any of the known helper viruses such as adenovirus, herpesvirus (other than herpes simplex virus type-1) and vaccinia virus.

The term "accessory function vector" refers generally to a nucleic acid molecule that includes nucleotide sequences providing accessory functions. An accessory function vector can be transfected into a suitable host cell, wherein the vector is then capable of supporting AAV virion production in the host cell. Expressly excluded from the term are infectious viral particles as they exist in nature, such as adenovirus, herpesvirus or vaccinia virus particles. Thus, accessory function vectors can be in the form of a plasmid, phage, transposon or cosmid. In particular, it has been demonstrated that the full-complement of adenovirus genes are not required for accessory helper functions. For example, adenovirus mutants incapable of DNA replication and late gene synthesis have been shown to be permissive for AAV replication. Ito et al., (1970) *J. Gen. Virol.* 9:243; Ishibashi et al, (1971) *Virology* 45:317. Similarly, mutants within the E2B and E3 regions have been shown to support AAV replication, indicating that the E2B and E3 regions are probably not involved in providing accessory functions. Carter et al., (1983) *Virology* 126:505. However, adenoviruses defective in the E1 region, or having a deleted E4 region, are unable to support AAV replication. Thus, E1A and E4 regions are likely required for AAV replication, either directly or indirectly. Laughlin et al., (1982). *J. Virol.* 41:868; Janik et al., (1981) *Proc. Natl. Acad. Sci. USA* 78:1925; Carter et al., (1983) *Virology* 126:505. Other characterized Ad mutants include: E1B (Laughlin et al. (1982), supra; Janik et al. (1981), supra; Ostrove et al., (1980) *Virology* 104:502); E2A (Handa et al., (1975) *J. Gen. Virol.* 29:239; Strauss et al., (1976) *J. Virol.* 17:140; Myers et al., (1980) *J. Virol.* 35:665; Jay et al., (1981) *Proc. Natl. Acad. Sci. USA* 78:2927; Myers et al., (1981) *J. Biol. Chem.* 256:567); E2B (Carter, *Adeno-Associated Virus Helper Functions, in I CRC Handbook of Parvoviruses* (P. Tijssen ed., 1990)); E3 (Carter et al. (1983), supra); and E4 (Carter et al. (1983), supra; Carter (1995)). Although studies of the accessory functions provided by adenoviruses having mutations in the E1B coding region have produced conflicting results, Samulski et al., (1988) *J. Virol.* 62:206-210, recently reported that E1B55k is required for AAV virion production, while E1B19k is not. In addition, International Publication WO 97/17458 and Matshushita et al., (1998) *Gene Therapy* 5:938-945, describe accessory function vectors encoding various Ad genes. Particularly preferred accessory function vectors comprise an adenovirus VA RNA coding region, an adenovirus E4 ORF6 coding region, an adenovirus E2A 72 kD coding region, an adenovirus E1A coding region, and an adenovirus E1B region lacking an intact E1B55k coding region. Such vectors are described in International Publication No. WO 01/83797.

By "recombinant virus" is meant a virus that has been genetically altered, e.g., by the addition or insertion of a heterologous nucleic acid construct into the particle.

By "AAV virion" is meant a complete virus particle, such as a wild-type (wt) AAV virus particle (comprising a linear, single-stranded AAV nucleic acid genome associated with an AAV capsid protein coat). In this regard, single-stranded AAV nucleic acid molecules of either complementary sense, e.g., "sense" or "antisense" strands, can be packaged into any one AAV virion and both strands are equally infectious.

The terms "recombinant AAV virion," "rAAV virion," "AAV vector particle," "full capsids," "fulls," and "full particles" are defined herein as an infectious, replication-defective virus including an AAV protein shell, encapsidating a heterologous nucleotide sequence of interest which is flanked on both sides by AAV ITRs. A rAAV virion is produced in a suitable host cell which has had sequences specifying an AAV vector, AAV helper functions and accessory functions introduced therein. In this manner, the host cell is rendered capable of encoding AAV polypeptides that are required for packaging the AAV vector (containing a recombinant nucleotide sequence of interest) into infectious recombinant virion particles for subsequent gene delivery.

The terms "empty capsid," "empty particle," and "empties" refer to an AAV virion that includes an AAV protein shell but that lacks in whole or part the polynucleotide construct comprising the heterologous nucleotide sequence of interest flanked on both sides by AAV ITRs. Accordingly, the empty capsid does not function to transfer the gene of interest into the host cell.

The term "host cell" denotes, for example, microorganisms, yeast cells, insect cells, and mammalian cells, that can be, or have been, used as recipients of an AAV helper construct, an AAV vector plasmid, an accessory function vector, or other transfer DNA. The term includes the progeny of the original cell which has been transfected. Thus, a "host cell" as used herein generally refers to a cell which has been transfected with an exogenous DNA sequence. It is understood that the progeny of a single parental cell may not necessarily be completely identical in morphology or in genomic or total DNA complement as the original parent, due to natural, accidental, or deliberate mutation.

The term "transfection" is used to refer to the uptake of foreign DNA by a cell, and a cell has been "transfected" when exogenous DNA has been introduced inside the cell membrane. A number of transfection techniques are generally known in the art. See, e.g., Graham et al. (1973) *Virology*, 52:456, Sambrook et al. (1989) *Molecular Cloning, a laboratory manual*, Cold Spring Harbor Laboratories, New York, Davis et al. (1986) *Basic Methods in Molecular Biology*, Elsevier, and Chu et al. (1981) *Gene* 13:197. Such techniques can be used to introduce one or more exogenous DNA moieties into suitable host cells.

As used herein, the term "cell line" refers to a population of cells capable of continuous or prolonged growth and division in vitro. Often, cell lines are clonal populations derived from a single progenitor cell. It is further known in the art that spontaneous or induced changes can occur in karyotype during storage or transfer of such clonal populations. Therefore, cells derived from the cell line referred to may not be precisely identical to the ancestral cells or cultures, and the cell line referred to includes such variants.

A stock or preparation of rAAV virions comprising AAV vector particles (packaged genomes) is "substantially free of" AAV empty capsids when at least about 50%-99% or more of the virions present in the stock are rAAV virions with packaged genomes (i.e., AAV vector particles). Preferably, the AAV vector particles comprise at least about 75% to 85%, more preferably about 90% of the virions present in the stock, even more preferably at least about 95%, or even 99% or more by weight of the virions present in the stock, or any integer between these ranges. Thus, a stock is substantially free of AAV empty capsids when from about 40% to about 1% or less, preferably about 25% to about 15% or less, more preferably about 10% or less, even more preferably about 5% to about 1% or less of the resulting stock comprises empty capsids.

A "nucleic acid" sequence refers to a DNA or RNA sequence. The term captures sequences that include any of the known base analogues of DNA and RNA such as, but not limited to 4-acetylcytosine, 8-hydroxy-N6-methyladenosine, aziridinylcytosine, pseudoisocytosine, 5-(carboxyhydroxylmethyl) uracil, 5-fluorouracil, 5-bromouracil, 5-carboxymethylaminomethyl-2-thiouracil, 5-carboxymethylaminomethyluracil, dihydrouracil, inosine, N6-isopentenyladenine, 1-methyladenine, 1-methylpseudouracil, 1-methylguanine, 1-methylinosine, 2,2-dimethylguanine, 2-methyladenine, 2-methylguanine, 3-methylcytosine, 5-methylcytosine, N6-methyladenine, 7-methylguanine, 5-methylaminomethyluracil, 5-methoxyaminomethyl-2-thiouracil, beta-D-mannosylqueosine, 5'-methoxycarbonylmethyluracil, 5-methoxyuracil, 2-methylthio-N6-isopentenyladenine, uracil-5-oxyacetic acid methylester, uracil-5-oxyacetic acid, oxybutoxosine, pseudouracil, queosine, 2-thiocytosine, 5-methyl-2-thiouracil, 2-thiouracil, 4-thiouracil, 5-methyluracil, Buracil-5-oxyacetic acid methylester, uracil-5-oxyacetic acid, pseudouracil, queosine, 2-thiocytosine, and 2,6-diaminopurine.

A "coding sequence" or a sequence which "encodes" a selected polypeptide, is a nucleic acid molecule which is transcribed (in the case of DNA) and translated (in the case of mRNA) into a polypeptide in vivo when placed under the control of appropriate regulatory sequences. The boundaries of the coding sequence are determined by a start codon at the 5' (amino) terminus and a translation stop codon at the 3' (carboxy) terminus. A transcription termination sequence may be located 3' to the coding sequence.

The term DNA "control sequences" refers collectively to promoter sequences, polyadenylation signals, transcription termination sequences, upstream regulatory domains, origins of replication, internal ribosome entry sites ("IRES"), enhancers, and the like, which collectively provide for the replication, transcription and translation of a coding sequence in a recipient cell. Not all of these control sequences need always be present so long as the selected coding sequence is capable of being replicated, transcribed and translated in an appropriate host cell.

The term "promoter" is used herein in its ordinary sense to refer to a nucleotide region comprising a DNA regulatory sequence, wherein the regulatory sequence is derived from a gene which is capable of binding RNA polymerase and initiating transcription of a downstream (3'-direction) coding sequence. Transcription promoters can include "inducible promoters" (where expression of a polynucleotide sequence operably linked to the promoter is induced by an analyte, cofactor, regulatory protein, etc.), "repressible promoters" (where expression of a polynucleotide sequence operably linked to the promoter is induced by an analyte, cofactor, regulatory protein, etc.), and "constitutive promoters."

"Operably linked" refers to an arrangement of elements wherein the components so described are configured so as to perform their usual function. Thus, control sequences operably linked to a coding sequence are capable of effecting the expression of the coding sequence. The control sequences need not be contiguous with the coding sequence, so long as they function to direct the expression thereof. Thus, for example, intervening untranslated yet transcribed sequences can be present between a promoter sequence and the coding sequence and the promoter sequence can still be considered "operably linked" to the coding sequence.

For the purpose of describing the relative position of nucleotide sequences in a particular nucleic acid molecule throughout the instant application, such as when a particular nucleotide sequence is described as being situated "upstream," "downstream," "3'," or "5'" relative to another sequence, it is to be understood that it is the position of the sequences in the "sense" or "coding" strand of a DNA molecule that is being referred to as is conventional in the art.

The term "heterologous" as it relates to nucleic acid sequences such as coding sequences and control sequences, denotes sequences that are not normally joined together, and/or are not normally associated with a particular cell. Thus, a "heterologous" region of a nucleic acid construct or a vector is a segment of nucleic acid within or attached to another nucleic acid molecule that is not found in association with the other molecule in nature. For example, a heterologous region of a nucleic acid construct could include a coding sequence flanked by sequences not found in association with the coding sequence in nature. Another example of a heterologous coding sequence is a construct where the coding sequence itself is not found in nature (e.g., synthetic sequences having codons different from the native gene). Similarly, a cell transformed with a construct which is not normally present in the cell would be considered heterologous for purposes of this invention. Allelic variation or naturally occurring mutational events do not give rise to heterologous DNA, as used herein.

By "isolated" when referring to a nucleotide sequence, is meant that the indicated molecule is present in the substantial absence of other biological macromolecules of the same type. Thus, an "isolated nucleic acid molecule which encodes a particular polypeptide" refers to a nucleic acid molecule which is substantially free of other nucleic acid molecules that do not encode the subject polypeptide; however, the molecule may include some additional bases or moieties which do not deleteriously affect the basic characteristics of the composition.

2. MODES OF CARRYING OUT THE INVENTION

Before describing the present invention in detail, it is to be understood that this invention is not limited to particular formulations or process parameters as such formulations or process parameters may, of course, vary. It is also to be understood that the terminology used herein is for the purpose of describing particular embodiments of the invention only, and is not intended to be limiting.

Although a number of methods and materials similar or equivalent to those described herein can be used in the practice of the present invention, the preferred materials and methods are described herein.

The present invention involves reducing the numbers of, or eliminating, AAV empty capsids contained within purified stocks of AAV virions, with minimal loss to AAV vector particles contained therein. The methods of the present invention may be used regardless of the process in which rAAV virions are generated.

There are several methods that are well known in the art for generating rAAV virions: for example, transfection using vector and AAV helper sequences in conjunction with coinfection with one of the AAV helper viruses (e.g., adenovirus, herpesvirus, or vaccinia virus) or transfection with a recombinant AAV vector, an AAV helper vector, and an accessory function vector. For detailed descriptions of methods for generating rAAV virions see, U.S. Pat. Nos. 6,001,650 and 6,004,797, both incorporated herein by reference in their entireties.

For example, wild-type AAV and helper viruses may be used to provide the necessary replicative functions for producing rAAV virions (see, e.g., U.S. Pat. No. 5,139,941, incorporated herein by reference in its entirety). Alternatively, a plasmid, containing helper function genes, in combination with infection by one of the well-known helper viruses can be used as the source of replicative functions (see e.g., U.S. Pat. No. 5,622,856 and U.S. Pat. No. 5,139,941, both incorporated herein by reference in their entireties). Similarly, a plasmid, containing accessory function genes can be used in combination with infection by wild-type AAV, to provide the necessary replicative functions. These three approaches, when used in combination with a rAAV vector, are each sufficient to produce rAAV virions. Other approaches, well known in the art, can also be employed by the skilled artisan to produce rAAV virions.

In a preferred embodiment of the present invention, a triple transfection method (described in detail in U.S. Pat. No. 6,001,650, incorporated by reference herein in its entirety) is used to produce rAAV virions because this method does not require the use of an infectious helper virus, enabling rAAV virions to be produced without any detectable helper virus present. This is accomplished by use of three vectors for rAAV virion production: an AAV helper function vector, an accessory function vector, and a rAAV expression vector. One of skill in the art will appreciate, however, that the nucleic acid sequences encoded by these vectors can be provided on two or more vectors in various combinations.

As explained herein, the AAV helper function vector encodes the "AAV helper function" sequences (i.e., rep and cap), which function in trans for productive AAV replication and encapsidation. Preferably, the AAV helper function vector supports efficient AAV vector production without generating any detectable wt AAV virions (i.e., AAV virions containing functional rep and cap genes). An example of such a vector, pHLP19 is described in U.S. Pat. No. 6,001,650, incorporated herein by reference in its entirety. The rep and cap genes of the AAV helper function vector can be derived from any of the known AAV serotypes, as explained above. For example, the AAV helper function vector may have a rep gene derived from AAV-2 and a cap gene derived from AAV-6; one of skill in the art will recognize that other rep and cap gene combinations are possible, the defining feature being the ability to support rAAV virion production.

The accessory function vector encodes nucleotide sequences for non-AAV derived viral and/or cellular functions upon which AAV is dependent for replication (i.e., "accessory functions"). The accessory functions include those functions required for AAV replication, including, without limitation, those moieties involved in activation of AAV gene transcription, stage specific AAV mRNA splicing, AAV DNA replication, synthesis of cap expression products, and AAV capsid assembly. Viral-based accessory functions can be derived from any of the well-known helper viruses such as adenovirus, herpesvirus (other than herpes simplex virus type-1), and vaccinia virus. In a preferred embodiment, the accessory function plasmid pLadeno5 is used (details regarding pLadeno5 are described in U.S. Pat. No. 6,004,797, incorporated herein by reference in its entirety). This plasmid provides a complete set of adenovirus accessory functions for AAV vector production, but lacks the components necessary to form replication-competent adenovirus.

Once stocks of AAV virions are produced, a number of methods, detailed below, can be used to determine infectious titers and to purify AAV vector particles away from AAV empty capsids.

In order to further an understanding of the invention, a more detailed discussion is provided below regarding recombinant AAV expression vectors, AAV helper and accessory functions, compositions comprising AAV virions, as well as delivery of virions.

Recombinant AAV Expression Vectors

Recombinant AAV (rAAV) expression vectors are constructed using known techniques to provide as operatively linked components in the direction of transcription, control elements including a transcriptional initiation region, the polynucleotide of interest and a transcriptional termination region. The control elements are selected to be functional in the host cell of interest. The resulting construct which contains the operatively linked components is bounded (5' and 3') with functional AAV ITR sequences.

The nucleotide sequences of AAV ITR regions are known. See, e.g., Kotin, R. M. (1994) *Human Gene Therapy* 5:793-801; Berns, K. I. "Parvoviridae and their Replication" in *Fundamental Virology*, 2nd Edition, (B. N. Fields and D. M. Knipe, eds.) for the AAV-2 sequence. AAV ITRs used in the vectors of the invention need not have a wild-type nucleotide sequence, and may be altered, e.g., by the insertion, deletion or substitution of nucleotides. Additionally, AAV ITRs may be derived from any of several AAV serotypes, including without limitation, AAV-1, AAV-2, AAV-3, AAV-4, AAV-5, AAV-6, AAV-7 and AAV-8, etc. Furthermore, 5' and 3' ITRs which flank a selected nucleotide sequence in an AAV expression vector need not necessarily be identical or derived from the same AAV serotype or isolate, so long as they function as intended, i.e., to allow for excision and rescue of the sequence of interest from a host cell genome or vector, and to allow integration of the DNA molecule into the recipient cell genome when AAV Rep gene products are present in the cell.

Suitable polynucleotide molecules for use in AAV vectors will be less than about 5 kilobases (kb) in size. The selected polynucleotide sequence is operably linked to control elements that direct the transcription or expression thereof in the subject in vivo. Such control elements can comprise control sequences normally associated with the selected gene. Alternatively, heterologous control sequences can be employed. Useful heterologous control sequences generally include those derived from sequences encoding mammalian or viral genes. Examples include, but are not limited to, neuron-specific enolase promoter, a GFAP promoter, the SV40 early promoter, mouse mammary tumor virus LTR promoter; adenovirus major late promoter (Ad MLP); a herpes simplex virus (HSV) promoter, a cytomegalovirus (CMV) promoter such as the CMV immediate early promoter region (CMVIE), a rous sarcoma virus (RSV) promoter, the CAG promoter, synthetic promoters, hybrid promoters, and the like. In addition, sequences derived from nonviral genes, such as the murine metallothionein gene, will also find use herein. Such promoter sequences are commercially available from, e.g., Stratagene (San Diego, Calif.).

The AAV expression vector which harbors the polynucleotide molecule of interest bounded by AAV ITRs, can be constructed by directly inserting the selected sequence(s) into an AAV genome which has had the major AAV open reading frames ("ORFs") excised therefrom. Other portions of the AAV genome can also be deleted, so long as a sufficient portion of the ITRs remain to allow for replication and packaging functions. Such constructs can be designed using techniques well known in the art. See, e.g., U.S. Pat. Nos. 5,173,414 and 5,139,941; International Publication Nos. WO 92/01070 (published 23 Jan. 1992) and WO 93/03769 (published 4 Mar. 1993); Lebkowski et al. (1988) *Molec. Cell. Biol.* 8:3988-3996; Vincent et al. (1990) *Vaccines* 90 (Cold Spring Harbor Laboratory Press); Carter (1992) *Current Opinion in Biotechnology* 3:533-539; Muzyczka (1992) *Current Topics in Microbiol. and Immunol.*

158:97-129; Kotin (1994) *Human Gene Therapy* 5:793-801; Shelling and Smith (1994) *Gene Therapy* 1:165-169; and Zhou et al. (1994) *J. Exp. Med.* 179:1867-1875.

Alternatively, AAV ITRs can be excised from the viral genome or from an AAV vector containing the same and fused 5' and 3' of a selected nucleic acid construct that is present in another vector using standard ligation techniques, such as those described in Sambrook et al., supra. For example, ligations can be accomplished in 20 mM Tris-Cl pH 7.5, 10 mM MgCl2, 10 mM DTT, 33 µg/ml BSA, 10 mM-50 mM NaCl, and either 40 µM ATP, 0.01-0.02 (Weiss) units T4 DNA ligase at 0° C. (for "sticky end" ligation) or 1 mM ATP, 0.3-0.6 (Weiss) units T4 DNA ligase at 14° C. (for "blunt end" ligation). Intermolecular "sticky end" ligations are usually performed at 30-100 µg/ml total DNA concentrations (5-100 nM total end concentration). AAV vectors which contain ITRs have been described in, e.g., U.S. Pat. No. 5,139,941. In particular, several AAV vectors are described therein which are available from the American Type Culture Collection ("ATCC") under Accession Numbers 53222, 53223, 53224, 53225 and 53226.

For the purposes of the invention, suitable host cells for producing rAAV virions from the AAV expression vectors include microorganisms, yeast cells, insect cells, and mammalian cells, that can be, or have been, used as recipients of a heterologous DNA molecule and that are capable of growth in, for example, suspension culture, a bioreactor, or the like. The term includes the progeny of the original cell which has been transfected. Thus, a "host cell" as used herein generally refers to a cell which has been transfected with an exogenous DNA sequence. Cells from the stable human cell line, 293 (readily available through, e.g., the American Type Culture Collection under Accession Number ATCC CRL1573) are preferred in the practice of the present invention. Particularly, the human cell line 293 is a human embryonic kidney cell line that has been transformed with adenovirus type-5 DNA fragments (Graham et al. (1977) *J. Gen. Virol.* 36:59), and expresses the adenoviral E1a and E1b genes (Aiello et al. (1979) *Virology* 94:460). The 293 cell line is readily transfected, and provides a particularly convenient platform in which to produce rAAV virions.

AAV Helper Functions

Host cells containing the above-described AAV expression vectors must be rendered capable of providing AAV helper functions in order to replicate and encapsidate the nucleotide sequences flanked by the AAV ITRs to produce rAAV virions. AAV helper functions are generally AAV-derived coding sequences which can be expressed to provide AAV gene products that, in turn, function in trans for productive AAV replication. AAV helper functions are used herein to complement necessary AAV functions that are missing from the AAV expression vectors. Thus, AAV helper functions include one, or both of the major AAV ORFs, namely the rep and cap coding regions, or functional homologues thereof.

By "AAV rep coding region" is meant the art-recognized region of the AAV genome which encodes the replication proteins Rep 78, Rep 68, Rep 52 and Rep 40. These Rep expression products have been shown to possess many functions, including recognition, binding and nicking of the AAV origin of DNA replication, DNA helicase activity and modulation of transcription from AAV (or other heterologous) promoters. The Rep expression products are collectively required for replicating the AAV genome. For a description of the AAV rep coding region, see, e.g., Muzyczka, N. (1992) *Current Topics in Microbiol. and Immunol.* 158:97-129; and Kotin, R. M. (1994) *Human Gene Therapy* 5:793-801. Suitable homologues of the AAV rep coding region include the human herpesvirus 6 (HHV-6) rep gene which is also known to mediate AAV-2 DNA replication (Thomson et al. (1994) *Virology* 204:304-311).

By "AAV cap coding region" is meant the art-recognized region of the AAV genome which encodes the capsid proteins VP1, VP2, and VP3, or functional homologues thereof. These Cap expression products supply the packaging functions which are collectively required for packaging the viral genome. For a description of the AAV cap coding region, see, e.g., Muzyczka, N. and Kotin, R. M. (supra).

AAV helper functions are introduced into the host cell by transfecting the host cell with an AAV helper construct either prior to, or concurrently with, the transfection of the AAV expression vector. AAV helper constructs are thus used to provide at least transient expression of AAV rep and/or cap genes to complement missing AAV functions that are necessary for productive AAV infection. AAV helper constructs lack AAV ITRs and can neither replicate nor package themselves.

These constructs can be in the form of a plasmid, phage, transposon, cosmid, virus, or virion. A number of AAV helper constructs have been described, such as the commonly used plasmids pAAV/Ad and pIM29+45 which encode both Rep and Cap expression products. See, e.g., Samulski et al. (1989) *J. Virol.* 63:3822-3828; and McCarty et al. (1991) *J. Virol.* 65:2936-2945. A number of other vectors have been described which encode Rep and/or Cap expression products. See, e.g., U.S. Pat. No. 5,139,941.

AAV Accessory Functions

The host cell (or packaging cell) must also be rendered capable of providing nonAAV-derived functions, or "accessory functions," in order to produce rAAV virions. Accessory functions are nonAAV-derived viral and/or cellular functions upon which AAV is dependent for its replication. Thus, accessory functions include at least those nonAAV proteins and RNAs that are required in AAV replication, including those involved in activation of AAV gene transcription, stage specific AAV mRNA splicing, AAV DNA replication, synthesis of Cap expression products and AAV capsid assembly. Viral-based accessory functions can be derived from any of the known helper viruses.

In particular, accessory functions can be introduced into and then expressed in host cells using methods known to those of skill in the art. Typically, accessory functions are provided by infection of the host cells with an unrelated helper virus. A number of suitable helper viruses are known, including adenoviruses; herpesviruses such as herpes simplex virus types 1 and 2; and vaccinia viruses. Nonviral accessory functions will also find use herein, such as those provided by cell synchronization using any of various known agents. See, e.g., Buller et al. (1981) *J. Virol.* 40:241-247; McPherson et al. (1985) *Virology* 147:217-222; Schlehofer et al. (1986) *Virology* 152:110-117.

Alternatively, accessory functions can be provided using an accessory function vector as defined above. See, e.g., U.S. Pat. No. 6,004,797 and International Publication No. WO 01/83797, incorporated herein by reference in its entirety. Nucleic acid sequences providing the accessory functions can be obtained from natural sources, such as from the genome of an adenovirus particle, or constructed using recombinant or synthetic methods known in the art. As explained above, it has been demonstrated that the full-complement of adenovirus genes are not required for accessory helper functions. In particular, adenovirus mutants incapable of DNA replication and late gene synthesis have been shown to be permissive for AAV replication. Ito et al., (1970) *J. Gen. Virol.* 9:243; Ishibashi et al, (1971) *Virology* 45:317. Similarly, mutants within the E2B and E3 regions have been shown to support AAV replication, indicating that the E2B and E3 regions are probably not involved in providing accessory functions. Carter et al., (1983) *Virology* 126:505. However, adenoviruses defective in the E1 region, or having a deleted E4 region, are unable to support AAV replication. Thus, E1A and E4 regions are likely required for AAV replication, either directly or indirectly. Laughlin et al., (1982) *J. Virol.* 41:868; Janik et al., (1981) *Proc. Natl. Acad. Sci. USA* 78:1925; Carter et al., (1983) *Virology* 126:505. Other characterized Ad mutants include: E1B (Laughlin et al. (1982), supra; Janik et al. (1981), supra; Ostrove et al., (1980) *Virology* 104:502); E2A (Handa et al., (1975) *J. Gen. Virol.* 29:239; Strauss et al., (1976) *J. Virol.* 17:140; Myers et al., (1980) *J. Virol.* 35:665; Jay et al., (1981) *Proc. Natl. Acad. Sci. USA* 78:2927; Myers et al., (1981) *J. Biol. Chem.* 256:567); E2B (Carter, *Adeno-Associated Virus Helper Functions, in I CRC Handbook of Parvoviruses* (P. Tijssen ed., 1990)); E3 (Carter et al. (1983), supra); and E4 (Carter et al. (1983), supra; Carter (1995)). Although studies of the accessory functions provided by adenoviruses having mutations in the E1B coding region have produced conflicting results, Samulski et al., (1988) *J. Virol.* 62:206-210, recently reported that E1B55k is required for AAV virion production, while E1B19k is not. In addition, International Publication WO 97/17458 and Matshushita et al., (1998) *Gene Therapy* 5:938-945, describe accessory function vectors encoding various Ad genes. Particularly preferred accessory function vectors comprise an adenovirus VA RNA coding region, an adenovirus E4 ORF6 coding region, an adenovirus E2A 72 kD coding region, an adenovirus E1A coding region, and an adenovirus E1B region lacking an intact E1B55k coding region. Such vectors are described in International Publication No. WO 01/83797.

As a consequence of the infection of the host cell with a helper virus, or transfection of the host cell with an accessory function vector, accessory functions are expressed which transactivate the AAV helper construct to produce AAV Rep and/or Cap proteins. The Rep expression products excise the recombinant DNA (including the DNA of interest) from the AAV expression vector. The Rep proteins also serve to duplicate the AAV genome. The expressed Cap proteins assemble into capsids, and the recombinant AAV genome is packaged into the capsids. Thus, productive AAV replication ensues, and the DNA is packaged into rAAV virions.

Purification of rAAV Virions

Following recombinant AAV replication, rAAV virions can be purified from the host cell using a variety of conventional purification methods, such as column chromatography, CsCl gradients, and the like. For example, a plurality of column purification steps can be used, such as purification over an anion exchange column, an affinity column and/or a cation exchange column. See, for example, International Publication No. WO 02/12455. Further, if infection is employed to express the accessory functions, residual helper virus can be inactivated, using known methods. For example, adenovirus can be inactivated by heating to temperatures of approximately 60° C. for, e.g., 20 minutes or more. This treatment effectively inactivates only the helper virus since AAV is extremely heat stable while the helper adenovirus is heat labile.

Recombinant AAV vectors containing any number of reporter genes can be used to determine infectious titers. For example, alkaline phosphatase, β-galactosidase (LacZ), green fluorescent protein, or luciferase may be used. After harvesting the transfected host cell, a lysate is formed by disrupting the transfected host cells using techniques suitable for large-scale production, such as microfluidization. The lysate is then filtered (for example, through a 0.45 μm filter), and purified using column chromatographic methods as described herein. Other techniques have also been reported to determine the infectious titer of any AAV vector. See, e.g., Zhen et al., "An Infectious Titer Assay for Adeno-associated Virus (AAV) Vectors with Sensitivity Sufficient to Detect Single Infectious Events." *Hum. Gene Ther.* (2004) In Press.

The purified AAV stock is then treated to remove empty capsids using column chromatography techniques. In a particularly preferred method of the invention, rAAV preparations are obtained by lysing transfected cells to obtain a crude cell lysate. The crude cell lysate can then be clarified to remove cell debris by techniques well known in the art, such as filtering, centrifuging, and the like, to render a clarified cell lysate. The crude cell lysate or clarified cell lysate, which contain both AAV vector particles and AAV empty capsids, is then applied to a first cation exchange column under non-separating conditions. The first cation exchange column functions to further separate the AAV vector particles and the AAV empty capsids from cellular and other components present in the cell lysate preparation. Methods for performing the initial purification of the cell lysate are known. One representative method is described in U.S. Pat. No. 6,593,123, incorporated herein by reference in its entirety.

Fractions collected from the first cation exchange column are then applied to a second ion exchanger, i.e., a second cation exchange column and/or an anion exchange column, using different elution conditions that separate AAV empty capsids from AAV vector particles.

Suitable cation exchangers for both the first cation exchange column and the second cation exchange column, if used, include a wide variety of materials, known in the art. Particularly preferred are strong cation exchangers capable of binding rAAV virions over a wide pH range. For example carboxymethylated and sulfonated cation exchange matrices are particularly useful for use herein. Useful matrix materials include but are not limited to, cellulose matrices, such as fibrous, microgranular and beaded matrices; agarose, dextran, polyacrylate, polyvinyl, polystyrene, silica and polyether matrices; and composites. Particularly preferred herein are matrices containing the functional ligand R—$SO_3^-$, preferably sulfopropyl or sulfoethyl resins. Representative matrices include but are not limited to POROS HS, POROS SP, POROS S (all strong cation exchangers available from Applied Biosystems, Foster City, Calif.), POROS CM (weak cation exchanger available from Applied Biosystems, Foster City, Calif.), TOSOHAAS TOYOPEARL SP550C and MERCK FRACTOGEL EMD $SO_3^-$-650 (m), as well as SOURCE 15S, SOURCE 30S, SEPHAROSE SP FF, SEPHAROSE SP XL (all available from Amersham Bioscience, Piscataway, N.J.).

For all column chromatography protocols given below, columns can be prepared using standard protocols known in the art with the appropriate buffer solutions. Sample is then loaded. For the first cation exchange column used, conditions are such that both empty capsids and AAV vector particles bind to the column resin and are subsequently eluted together, but are separated from other cellular components and debris present in the cell lysate. For example, empty and full capsids are eluted using a buffer of appropriate ionic strength. Suitable buffers include e.g., 10-50 mM sodium phosphate, preferably 15-40, such as 15 . . . 20 . . . 25 . . . 30 . . . 35 . . . 40, etc. mM sodium phosphate containing salt, such as NaCl or KCl, at a concentration of e.g, 100-700 mM, such as 200-400 mM, e.g., 200 . . . 300 . . . 325 . . . 350 . . . 370 . . . 380 . . . 400, etc., or any concentration within these ranges. The pH of the buffer can be from about 3 to about 9.5, such as 4-8, e.g., pH 4 . . . 4.5 . . . 5 . . . 5.5 . . . 6, etc., or any pH within these ranges. The fractions are collected and then can be run either on an anion exchange column and/or a second cation exchange column under separating conditions.

If a second cation exchange column is used in a subsequent step to separate empty AAV capsids from AAV vector particles, two elution buffers are used, one low salt buffer and one high salt buffer. In particular, empty capsids are separated from AAV vector particles using an appropriate buffer at a pH of from about pH 6 to pH 12, preferably pH 7 to pH 10, and even more preferably pH 7.5 to pH 9.5, such as pH 7.5 . . . 8.0, 8.1, 8.2, 8.3, 8.4, 8.5 . . . 9.0, 9.1, 9.2, 9.3, 9.4, 9.5, or any pH between the stated ranges. Appropriate buffers are well known in the art and include, without limitation, buffers with the following buffer ions: acetic acid; malonic acid; MES; phosphate; HEPES, BICINE, and the like. To elute the sample, the ionic strength of the starting buffer is increased using a salt, such as NaCl, KCl, ammonia sulfate or any other salts containing sulfate, formate, acetate, citrate, and/or phosphate. In one embodiment of the invention, the column is first treated with a low salt concentration, e.g., 10-200 mM of ammonium acetate, such as 20 . . . 25 . . . 30 . . . 35 . . . 40 . . . 45 . . . 50 . . . 55 . . . 60 . . . 65 . . . 100 mM, or any concentration within these ranges. This treatment results in elution of AAV vector particles from the column resin. Subsequently the column is treated with a higher salt concentration in order to elute AAV empty capsids. One example for use as the second buffer is ammonium acetate with a concentration of 100-800 mM, preferably 500-700 mM, such as 500 . . . 550 . . . 600 . . . 650 . . . 700 . . . 800 mM, or any concentration within these stated ranges. Using these conditions, the AAV vector particles elute in the early fractions and the empty particles later.

As explained above, in an alternate method of the invention, the preparation from the first cation exchange column is applied to an anion exchange column either in place of or in addition to the second cation exchange column. If an anion exchange column is used in addition to the second cation exchange column, it can be used either prior or subsequent to the second cation exchange column. Moreover, a second anion exchange column can be used after the first anion exchange column. A number of suitable anion exchangers for use with the present invention are known and include without limitation, MACRO PREP Q (strong anion-exchanger available from BioRad, Hercules, Calif.); UNO-SPHERE Q (strong anion-exchanger available from BioRad, Hercules, Calif.); POROS 50HQ (strong anion-exchanger available from Applied Biosystems, Foster City, Calif.); POROS 50D (weak anion-exchanger available from Applied Biosystems, Foster City, Calif.); POROS 50PI (weak anion-exchanger available from Applied Biosystems, Foster City, Calif.); SOURCE 30Q (strong anion-exchanger available from Amersham Biosciences, Piscataway, N.J.); DEAE SEPHAROSE (weak anion-exchanger available from Amersham Biosciences, Piscataway, N.J.); Q SEPHAROSE (strong anion-exchanger available from Amersham Biosciences, Piscataway, N.J.).

The anion exchange column is first equilibrated using standard buffers and according to the manufacturer's specifications. For example, the column can be equilibrated with, e.g., a 5 to 50 mM, preferably 7-20 mM, such as 10 mM, sodium phosphate buffer. Sample is then loaded and two elution buffers are used, one low salt buffer and one high salt buffer. Fractions are collected following each of the low salt and high salt washes and protein is detected in the fractions using standard techniques, such as monitoring UV absorption at 260 and 280 nm. Using an anion exchanger, the protein peaks from the lower salt eluate contain AAV empty capsids and the higher salt fractions contain AAV vector particles.

In particular, on the anion exchange column, empty capsids can separated from AAV vector particles using an appropriate buffer at a pH of from about pH 5 to pH 12, preferably pH 6 to pH 10, and even more preferably pH 7 to pH 9.5, such as pH 7.1, 7.2, 7.3, 7.4 . . . 8.0, 8.1, 8.2, 8.3, 8.4, 8.5 . . . 9.0, 9.1, 9.2, 9.3, 9.4, 9.5, or any pH between the stated ranges. Appropriate buffers for use with the anion exchange columns are well known in the art and are generally cationic or zwitterionic in nature. Such buffers include, without limitation, buffers with the following buffer ions: N-methylpiperazine; piperazine; Bis-Tris; Bis-Tris propane; Triethanolamine; Tris; N-methyldiethanolamine; 1,3-diaminopropane; ethanolamine; acetic acid, and the like. To elute the sample, the ionic strength of the starting buffer is increased using a salt, such as NaCl, KCl, sulfate, formate or acetate, at an appropriate pH.

In one embodiment of the invention, the anion exchange column is first treated with a low salt concentration, e.g., 10-100 mM of NaCl, such as 10 . . . 20 . . . 25 . . . 30 . . . 35 . . . 40 . . . 45 . . . 50 . . . 55 . . . 60 . . . 65 . . . 100 mM, or any concentration within these ranges. Following initial treatment, the column is then treated with a higher salt concentration in order to elute empty capsids, such as a higher NaCl concentration, or with another buffer with a greater ionic strength. One example for use as the second buffer is a sodium acetate buffer or a Tris-based buffer with a concentration of 100-300 mM, preferably 125-200 mM, such as 125 . . . 130 . . . 140 . . . 150 . . . 160 . . . 170 . . . 180 . . . 190 . . . 200 mM, or any concentration within these stated ranges. After the empty capsids are eluted from the column, the AAV vector particles can be recovered using a higher concentration of salt. One example for use as the elution buffer is 10 mM Tris buffer containing sodium acetate at a concentration in the range of 100-500 mM, preferably 130-300 mM, such as 100 . . . 130 . . . 150 . . . 200 . . . 250 . . . 300 . . . 350 . . . 400 . . . 450 . . . 500 mM, or any concentration within these stated ranges.

Using the techniques described above, more than 90% of the AAV empty capsids can be separated away from the AAV vector particles. Moreover, high recovery of AAV vector particles is readily achieved, i.e., more than 10%, preferably more than 25%, even more preferably more than 50%, such as more than 60% of the AAV vector particles can be recovered.

Methods for assaying for empty capsids and AAV vector particles with packaged genomes are known in the art. See, e.g., Grimm et al., *Gene Therapy* (1999) 6:1322-1330; Sommer et al., *Molec. Ther.* (2003) 7:122-128. To test for denatured capsid, the methods include subjecting the treated AAV stock to SDS-polyacrylamide gel electrophoresis, consisting of any gel capable of separating the three capsid proteins, for example, a gradient gel containing 3-8% Tris-acetate in the buffer, then running the gel until sample material is separated, and blotting the gel onto nylon or nitrocellulose membranes, preferably nylon. Anti-AAV capsid antibodies are then used as the primary antibodies that bind to denatured capsid proteins, preferably an anti-AAV capsid monoclonal antibody, most preferably the B1 anti-AAV-2 monoclonal antibody (Wobus et al., *J. Virol.* (2000) 74:9281-9293). A secondary antibody is then used, one that binds to the primary antibody and contains a means for detecting binding with the primary antibody, more preferably an anti-IgG antibody containing a detection molecule covalently bound to it, most preferably a sheep anti-mouse IgG antibody covalently linked to horseradish peroxidase. A method for detecting binding is used to semi-quantitatively determine binding between the primary and secondary antibodies, preferably a detection method capable of detecting radioactive isotope emissions, electromagnetic radiation, or colorimetric changes, most preferably a chemiluminescence detection kit.

To test for infectious titer, the methods include the seeding of about 100,000 host cells, preferably of human origin, most preferably HeLa cells, into tissue culture-treated plates, preferably 24-well tissue culture-treated plates, and incubated for about 24 hours after which adenovirus, preferably the adenovirus-2 serotype, and treated rAAV stock is added to the host cells. The host cells, adenovirus, and rAAV stock are allowed to incubate for 24 hours, after which the host cells are fixed, preferably with formaldehyde and glutaraldehyde, and stained with an appropriate agent that will detect the rAAV expressed transgene; for example, with rAAV-LacZ, X-gal is contemplated as the staining agent. Other agents for other reporter genes are well known in the art. More general methods to determine infectivity titers of vectors containing any transgene are also known in the art. See, e.g., Zhen et al., "An Infectious Titer Assay for Adeno-associated Virus (AAV) Vectors with Sensitivity Sufficient to Detect Single Infectious Events." *Hum. Gene Ther.* (2004) In Press.

3. EXPERIMENTAL

Below are examples of specific embodiments for carrying out the present invention. The examples are offered for illustrative purposes only, and are not intended to limit the scope of the present invention in any way.

Efforts have been made to ensure accuracy with respect to numbers used (e.g., amounts, temperatures, etc.), but some experimental error and deviation should, of course, be allowed for.

Material and Methods:
rAAV Production and Purification:

Recombinant AAV virions containing the gene encoding human factor IX (rAAV-hFIX) were produced by the triple-transfection method described in U.S. Pat. Nos. 6,001,650 and 6,004,797, both incorporated herein by reference in their entireties. The plasmids used were the accessory function plasmid 'pladeno5', the AAV helper function plasmid 'pHLP19', and the recombinant AAV plasmid 'phFIX-16'. Human embryonic kidney (HEK) 293 cells were used as host cells for the production of rAAV virions.

The transfected 293 cells were harvested approximately 72 hours post-transfection and disrupted by microfluidization using a Microfluidizer™ (Microfluidics International Corp., Newton, Mass.) and the crude lysate was collected and filtered through serial filters to remove cell debris to create a clarified cell lysate. The clarified cell lysate containing packaged and empty capsids was then loaded on a POROS 50HS column to purify AAV vector particles and AAV empty capsids from other cellular components. The AAV vector particles and empty capsids were eluted from the POROS 50HS column using a buffer containing 20 mM sodium phosphate, 370 mM NaCl, pH 5.5. The AAV preparation containing both AAV vector particles and empty capsids was diluted 2-fold to reduce the salt concentration and further purified through a Q SEPHAROSE column, the flow-through AAV vector particles and empty capsids were collected, and concentration and buffer exchange was performed using ultra-filtration and dialfiltration techniques.

The final POROS 50HS column-purified product contained both AAV empty capsids as well as AAV vector particles containing recombinant vector genomes. In order to generate control samples for each, cesium chloride was added to the POROS 50HS column-purified material to a density of 1.41 g/ml with mixing, and then subjected to ultracentrifugation at 45,000 rpm using a Ti 70 rotor for 23 hours. The visible empty and AAV vector particle bands were drawn using syringes separately. The purified empty capsids and AAV vector particles were separately dialyzed against buffer composed of 10 mM sodium phosphate pH 7.4, 140 mM NaCl and 5% sorbital using dialysis cassettes (Pierce) at 4° C. with three buffer exchanges.

Resins and Column Chromatography:

Various types of chromatography resins including anion exchange, cation exchange resins, a chromatofocusing resin and hydrophobic interaction (HIC) resins, were tested for their potential to separate AAV empty capsids and AAV vector particles. A high-throughput manifold was used for resin screening. Resins were packed into a disposable empty column with bed height of 3 cm (Bio-Rad Laboratories) that were installed on a manifold. The columns were equilibrated using buffer containing 10 mM sodium phosphate. The 0.2 µm filtered clarified HEK293 cell lysate AAV vectors and empty capsids were then diluted in column equilibration buffer a NaCl (salt) concentration of 50 mM and then loaded on the columns. The columns were washed with the equilibration buffer first and further washed with buffer containing 10 mM sodium phosphate and 40 mM NaCl pH 7.4 (low salt wash) to wash away unbound materials. Columns were then treated with elution buffer containing 10 mM sodium phosphate and 1 M NaCl (high salt wash). The materials washed off using the low salt wash were collected as one fraction, and the materials eluted using high salt wash as a separate fraction.

Following the initial screening using disposable columns, larger scale column chromatography, performed on a BIO-CAD 700 (Applied Biosystems), was used to further investigate promising resins and conditions. XK16 Glass columns (Amersham Pharmacia) were packed with different resins using constant flow packing methods with a linear velocity of 150 cm/hour. Chromatography parameters were programmed using various methods (see the details in each experiment result). In general, the programs contain functional blocks of column equilibration, sample loading, low salt washing, linear or step gradient and high salt cleaning step. The AAV vector particles and empty capsids eluted in various fractions were monitored and analyzed using the techniques described below.

SDS-PAGE and Western Blotting:

Samples from column fractions were taken and were heated in SDS-PAGE loading buffer containing reducing agent (DTT), and capsid proteins were resolved on pre-cast gradient polyacylamide gels (Novex). Silver staining was performed using SilverXpress (Invitrogen, Calif.) according to the manufacturer's instructions. Similarly, Western blot analysis was performed following transfer of proteins resolved by SDS-PAGE to nitrocellulose membranes. A monoclonal antibody (B1, American Research Products, MA) was used as the primary antibody to detect AAV capsid proteins (VP1, VP2, and VP3) by Western blot. Sheep anti-mouse IgG HRP conjugated (Promega, WI) was used as secondary antibody and detected by ECL kit (Amersham, UK).

Quantitative Real-Time PCR

The concentration of AAV vector genomes (vg) in column fractions was measured by quantitative real time PCR (Q-PCR). Samples were diluted and digested with DNase I to remove exogenous DNA. After inactivation of the DNase, the samples were further diluted and amplified using primers and a TaqMan™ fluorogenic probe specific for the DNA sequence between the primers. The number of cycles required to reach a defined level of fluorescence (threshold cycle, Ct) was measured for each sample on an Applied Biosystems Prsim 7700 Sequence Detection System. Plasmid DNA containing identical sequences to that contained in the AAV vector was employed to generate a standard curve in the Q-PCR reaction. The Ct values obtained from the samples were used to determine vector genome titer by normalizing it to the Ct value of the plasmid standard curve.

Example 1

Binding Properties of Empty Capsids and AAV Vector Particles with Packaged Genomes To test if AAV vector particles bound to anion exchange columns, several resins were screened using a high-throughput manifold technique. The cell lysate of the 293 cell culture containing AAV vector particles and empty capsids was diluted using 20 mM sodium phosphate buffer to reduce the NaCl concentration to about 50 mM and loaded on each column. The columns were then washed and eluted following the procedure described above. The collected samples were subjected to Western Blot to detect the AAV particles distribution in the fractions. As shown in FIGS. 1A and 1B, the AAV capsid protein-specific monoclonal antibody detected proteins in high salt (1M NaCl) elution fractions only (FIG. 1, lane 3, 5, 7 and 9). This data clearly indicated the both AAV vector particles and empty capsids bound to all of the anionic exchange resins (both weak and strong exchangers) screened.

Example 2

Charge Differences Between Empty Capsids and AAV Vector Particles

AAV empty capsids and AAV vector particles were separated using CsCl gradient centrifugation. The empty capsids resulted in a visible band at a lower salt density (about 1.3 gm/cc) and the AAV vector particles distributed as a visible band at a higher salt density (1.38-1.41 gm/cc). The empty capsids and AAV vector particles were prepared as described above and loaded on columns separately. Three resins, Q SEPHAROSE, POROS 50HQ and UNOSPHERE Q, were used for column chromatography runs which were performed using the same programs to compare the elution profiles between empty and full particles. AAV empty capsids eluted at a lower salt concentration (eluted in earlier fractions) as compared with the AAV vector particles (eluted in later fractions); this phenomenon was observed for all three anionic resins tested. In the case of the UNOSPHERE Q resin, the empty capsids were eluted in fraction 10 in a salt gradient from 0 to 500 mM NaCl, while the AAV vector particles eluted in fraction 11; in the case of the Q SEPHAROSE column, the empty capsids were eluted in fractions 11, 12 and 13 while the AAV vector particles were eluted in fractions of 13, 14 and 15. The same phenomenon was observed with the POROS 50HQ column when a more shallow gradient of sodium acetate concentration was used; the empty capsids were eluted in fractions 30 to 36, while the AAV vector particles eluted in fractions 36 to 40. These data clearly indicate that there are fundamental charge differences between AAV empty capsids and the AAV vector particles and that the two populations may be separated using these properties by column chromatographic techniques. Confirming the separation of empty capsids and AAV vector particles by these resins, the ratio of the UV absorption at 260 nm/280 nm gradually increased in eluted fractions, consistent with differential elution (empty capsids, which have a lower 260/280 ratio because they lack DNA, eluting first).

Example 3

Effect of Resins and Salts on the Elution Efficiency and Resolution Between Empty Capsids and AAV Vector Particles The resins screened in this process were all anionic exchange resins, but did exhibit differences (charge density, bead size and composition, etc.). The efficiency in binding and separating empty capsids and AAV vector particles varied from resin to resin. The empty capsids eluted using 110 mM NaCl in the Q SEPHAROSE column. In contrast, approximately 65 mM NaCl was sufficient to elute the empty capsids using the UNOSPHERE column, and in the case of the POROS HQ column, approximately 130 mM NaCl was sufficient to elute the empty capsids.

Several different salts were also used to in the studies of elution profiles. Sodium chloride, sodium acetate, potassium acetate, ammonium acetate and sodium citrate were subjected to side-by-side comparisons. Using the same program to perform the column chromatography runs, empty capsid elution was delayed for several fractions when sodium acetate or ammonium acetate were used in comparison with sodium chloride, suggesting that different salts have different properties in the anionic column chromatography and these properties may be used to enhance resolution in separation of empty capsid from the AAV vector particles.

Example 4

Defining Elution Conditions for Empty Capsids

Based on the experimental data discussed above, the POROS 50HQ resin was used to develop a column chromatography-based technique to separate empty capsids from AAV vector particles. Empty capsids prepared using CsCl centrifugation as described above were loaded on a column packed with POROS 50HQ resin. In separate runs, following low salt (50 mM NaCl) initial washing steps, the column was washed with either 150 mM sodium acetate, 160 mM sodium acetate or 170 mM sodium acetate. The empty capsids were eluted most efficiently when 170 mM NaAc was used. In a separate chromatography run using the same salt elution profile, purified AAV vector particles remained on the column and were then eluted when a linear salt concentration using higher concentration of sodium chloride was applied.

Example 5

Separation of Empty Capsids from AAV Vector Particles Using Anion Exchange Chromatography To demonstrate that empty capsids and AAV vector particles could be separated using column chromatography techniques, purified empty capsids and AAV vector particles were mixed together to generate samples containing both empty capsids and AAV vector particles. 3 ml of empty capsids with a concentration of 9E+13 particle/ml were mixed with 2 ml of full particles with the concentration of 7E+12 vector genomes (vg)/ml. The materials were further diluted 3-fold using 20 mM sodium phosphate buffer at pH 7.4. 14 ml of this diluted material was loaded on to a POROS 50HQ column with a 20 mL bed volume. The column chromatography elution profile described above was used, and the data indicated that the empty capsids were eluted in the salt condition of 170 mM sodium acetate while the AAV vector particles remained on the column and were then eluted using a linear gradient of NaCl salt. The UV absorption pattern (260:280 nm ratio) of material eluted from the column over the course of the separation was fully consistent with and further demonstrated the effective separation of the empty capsids from the AAV vector particles. The various fractions eluted from the column were further analyzed using capsid ELISA, Q-PCR, SDS-PAGE and OD analysis. All of the data obtained indicated that the separation of the empty capsids from AAV vector particles was complete and that the ratio of particles to vector genomes in the AAV vector particle fraction was 1:1. Thus, the AAV vector particles were completely separated from the empty capsids, despite starting material (loaded on the column) containing approximately 16-fold more empty capsids than vector particles (FIG. 2).

Example 6

Effect of pH on Separation of Empty Capsids from AAV Vector Particles Using Anion Exchange Chromatography To develop a complete column-based purification process to remove empty capsids, virions recovered from a cation exchange column (POROS HS) containing both empty capsids and AAV vector particles were applied to the POROS 50HQ column. When a similar method to separate empty capsids and AAV vector particles from CsCl purified samples was used, a clear separation as observed for the CsCl-gradient pre-purified and mixed samples was not obtained, although the two particle types remained distinguishable i.e. partial but incomplete separation of empty capsids and AAV vector particles was observed. Several parameters that may affect the resolution of column chromatography were tested to optimize the separation efficiency. Among parameters tested, it was found that pH enhanced the separation resolution significantly. Buffers with pH 7.4, pH 8.0, pH 8.5 and pH 9.0 were tested. The empty AAV capsids were selectively removed in the early fractions from the column when higher pHs, such as pH 9.0, were used in the process, while the AAV vector particles eluted in a higher salt concentration in the later fractions. Using pH 9.0, the empty capsids were removed as a single peak with the UV absorption signature pattern of higher UV 280 signal and lower UV 260 signal. In contrast, the second peak contained AAV vector particles and showed the opposite UV absorption pattern, UV 260 dominating UV 280, than expected for the DNA containing full AAV vector particle. The observation was further confirmed by Q-PCR and SDS-PAGE assays, indicating that the second peak contained AAV vector particles and the first peak empty capsids.

Example 7

Procedure to Separate AAV Empty Capsids from AAV Vector Particles Using Anion Exchange Column Chromatography Based on the observation described above, a procedure was designed to separate AAV empty capsids from the AAV vector particles using a Tris-based buffer at pH 8.5 and a POROS 50HQ column resin in an XK-16 glass column (Amersham Bioscience, Piscataway, N.J.). The materials eluted in early segments contained empty capsids and later segments AAV vector particles as indicated by the UV absorption patterns. This was further confirmed by Q-PCR analysis. The vectors that eluted at the higher salt concentration were analyzed on SDS-PAGE to determine purity. Vector genomes were determined by Q-PCR and replicate samples were loaded on SDS-PAGE and stained by silver staining. To serve as a control, rAAV virions containing AAV vector particles only were purified using CsCl centrifugation techniques and the same vector genomes were run on the SDS-PAGE gels.

Figure 3:
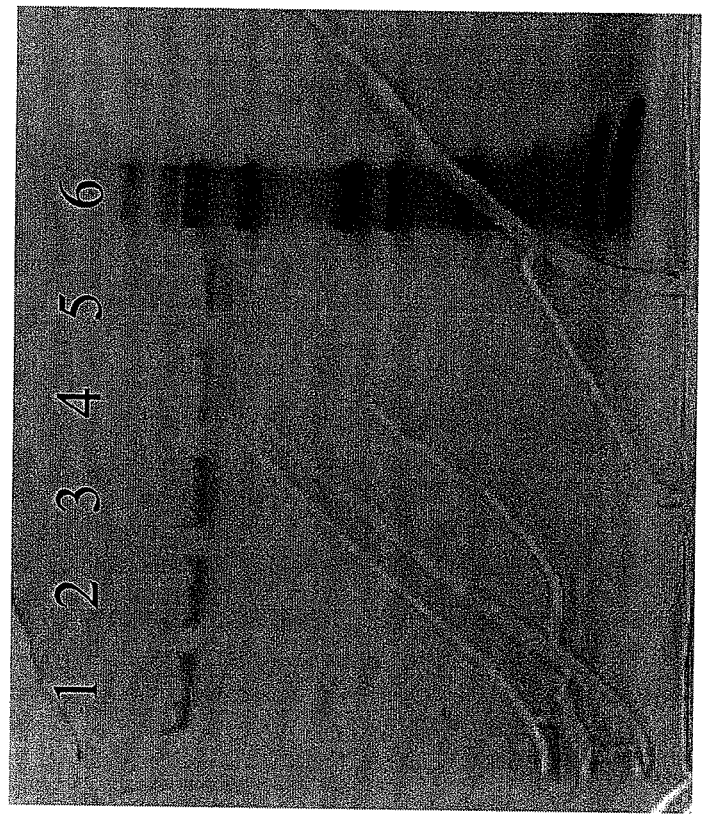
FIG. 3 is a depiction of a silver-stained SDS-PAGE gel of fractions from an anion exchange column as detailed in the examples. Lane 1: AAV vector particles; Lanes 2-5: vector elution fractions; Lane 6: protein molecular weight standards.

Using these techniques, approximately 60% of the vector was recovered. The vector recovered was essentially free of empty capsids (<10 of the particles were empty capsids) based on the SDS-PAGE silver staining analysis (FIG. 3). As shown in FIG. 3, there were no significant differences in the band density (corresponding to total protein) between the empty capsid free vector control (lane1) and the vector contained in eluted fractions from the column (lanes 2-5), when all lanes were loaded with an equal number of vector genomes.

Example 8

Separation of Empty Capsids from AAV Vector Particles Using Cation Exchange Column Chromatography Cation exchange column chromatography was also investigated for its potential to separate empty capsids from AAV vector particles. The AAV preparation from the first cation exchange column (described in the materials and methods section) containing both empty capsids and AAV vector particles, was applied to a POROS HS resin. The column was first equilibrated with 20 mM sodium phosphate buffer containing 200 mM NaCl at pH 7.4. The AAV preparation containing both AAV vector particles and empty capsids obtained from the first cation exchange column was diluted using 20 mM sodium phosphate, pH 7.4 to reduce the salt concentration to approximately 200 mM NaCl. This material was then loaded onto the POROS HS column. A gradient from 500 to 700 mM ammonium acetate containing 10 mM Tris at pH 8.5 was then applied to the column. Using this gradient elution protocol, the AAV vector particles eluted first, and were efficiently separated from the empty capsids which eluted subsequently at a higher ammonium acetate concentration. This contrasts to the separation observed using the anion exchange resin (Example 7 above) in which the empty capsids were eluted at a lower salt concentration relative to the AAV vector particles.

Figure 4:
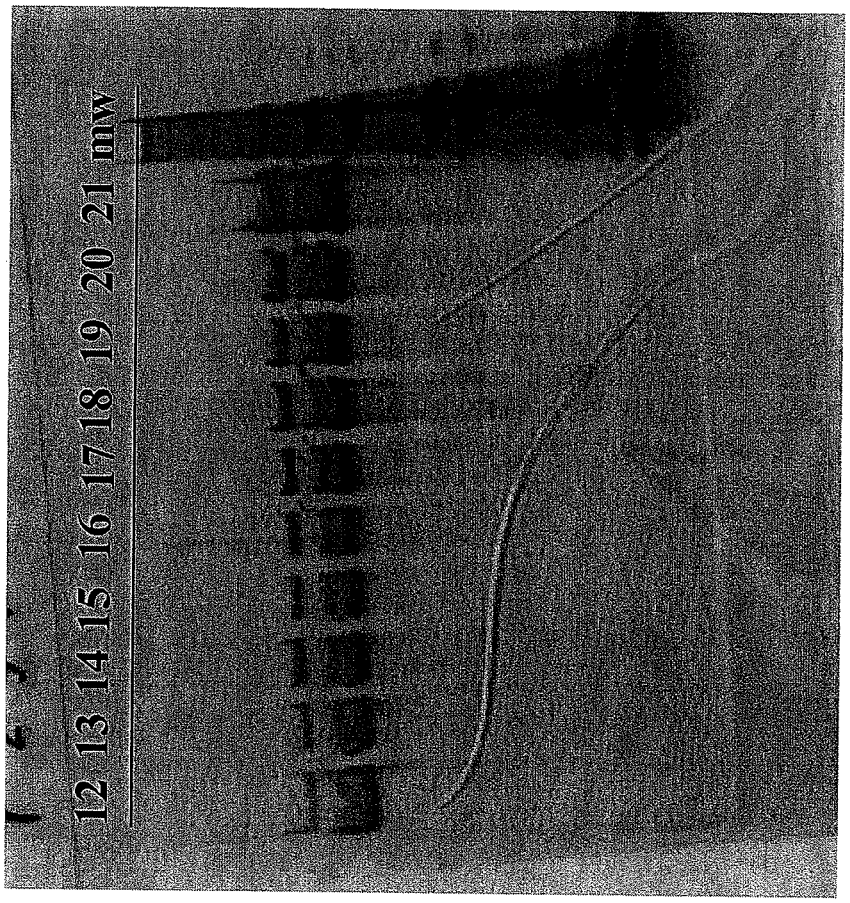
FIG. 4 is a depiction of a silver-stained SDS-PAGE gel showing elution fractions (Lanes 12-21) from a cation exchange column as described in the examples.

Additional information regarding the relative binding and elution patterns of the empty capsids and AAV vector particles on the cation exchange column was provided by the UV absorbance of the column eluate. For example, when the cation exchange column was run at pH 8.5, the chromatograph demonstrated a UV absorption pattern with 260 nm absorption (corresponding to AAV vector particles) dominant in the early fractions and 280 nm absorption (corresponding to empty capsids) dominant in the later elution fractions. As shown in FIG. 4, when the same vector genomes were subjected to SDS-PAGE silver staining analysis, the amount of protein increased significantly from early fractions to later fractions, indicating that early fractions contained less empty capsids.

Figure 5:
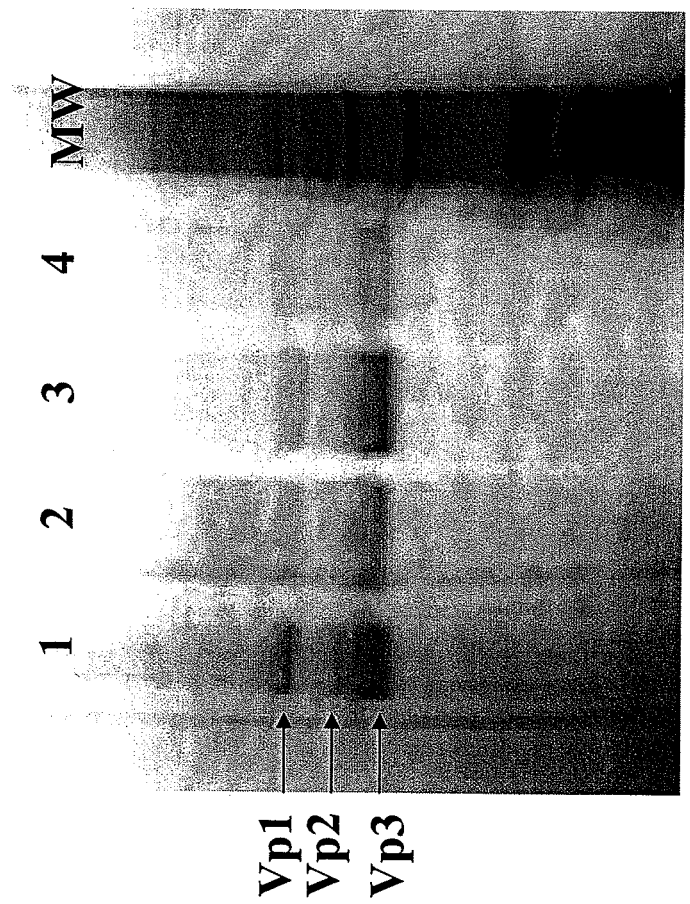
FIG. 5 is a depiction of a silver-stained SDS-PAGE gel showing separation of AAV empty particles from AAV vector particles using cation exchange column chromatography. Lane 1: starting material; Lanes 2-4: three independent samples of vectors eluted from cation exchange columns.

Based on these observations, separation of empty AAV capsids from AAV vector (DNA-containing) particles using cation exchange chromatography can be achieved. FIG. 5 shows an SDS-PAGE gel demonstrating separation. An AAV vector preparation containing both empty capsids and AAV vector particles eluted from a cation exchange column (in which conditions required to achieve separation were not used) were then loaded on a cation exchange column and eluted with a step gradient using ammonium acetate. Fractions containing vector genomes were identified using Q-PCR, and aliquots of these fractions were subjected to SDS-PAGE silver staining analysis. It is clear that the protein signals in the eluted fractions contained less protein signal per vg input relative to the material that was loaded onto the second column, demonstrating that empty capsids were removed from the AAV vector particles. Shown in lane 2 to 4 are the vectors eluted from three independent experiments, indicating consistently and repeatability of the observations.

Thus, methods for separating empty capsids from AAV vector particles are described. Although preferred embodiments of the subject invention have been described in some detail, it is understood that obvious variations can be made without departing from the spirit and the scope of the invention as defined by the appended claims.

We claim:

1. A method for purifying AAV vector particles from an AAV preparation comprising AAV vector particles and AAV empty capsids, to provide an AAV product substantially free of AAV empty capsids, said method comprising:
   (a) applying an AAV preparation comprising AAV vector particles and AAV empty capsids to a cation exchange chromatography column under conditions whereby said AAV vector particles and said AAV empty capsids bind the column;
   (b) adding a salt buffer to the column from (a) under conditions whereby AAV vector particles are eluted and AAV empty capsids remain bound to the column;
   (c) collecting eluted fractions from (b) that comprise AAV vector particles;
   (d) applying the fractions from step (c) to an anion exchange chromatography column under conditions whereby said AAV vector particles and AAV empty capsids, if present, bind the column;
   (e) adding a salt buffer to the column from (d) under conditions whereby AAV empty capsids are eluted and AAV vector particles remain bound to the column;
   (f) adding a buffer with a greater salt concentration relative to the buffer added in (e) to the column from (e) under conditions whereby AAV vector particles are eluted;
   (g) collecting eluted fractions from (f) and selecting fractions that consist essentially of AAV vector particles to provide an AAV product substantially free of AAV empty capsids, wherein AAV vector particles are present in said AAV product in an amount of at least 75%.

2. The method of claim 1, wherein said cation exchange column comprises a carboxymethylated or sulfonated matrix.

3. The method of claim 2, wherein said matrix comprises the functional ligand R—SO$_3$—.

4. The method of claim 1, wherein AAV vector particles are present in said AAV product in an amount of at least 85%.

5. The method of claim 1, wherein AAV vector particles are present in said AAV product in an amount of at least 90%.

6. The method of claim 1, wherein said AAV vector particles are derived from AAV-2.

7. The method of claim 1, wherein said AAV vector particles are derived from AAV-5.

8. The method of claim 1, further comprising:
   (h) applying the AAV preparation from (g) to a second anion exchange chromatography column under conditions whereby said AAV vector particles and said AAV empty capsids, if present, bind the column;
   (i) adding a salt buffer to the column from (h) under conditions whereby AAV empty capsids are eluted and AAV vector particles remain bound to the column;
   (j) adding a salt buffer with a greater salt concentration relative to the buffer added in (i) to the column from (i) under conditions whereby AAV vector particles are eluted;
   (k) collecting eluted fractions from (j) that comprise AAV vector particles to provide an AAV product substantially free of AAV empty capsids.

9. The method of claim 8, further comprising:
   (l) applying the AAV preparation from (k) to a second cation exchange chromatography column under conditions whereby said AAV vector particles and said AAV empty capsids bind the column;
   (m) adding a salt buffer to the column from (l) under conditions whereby AAV vector particles are eluted and AAV empty capsids remain bound to the column; and
   (o) collecting eluted fractions from (m) that comprise AAV vector particles to provide an AAV product substantially free of AAV empty capsids.

10. A method for purifying AAV vector particles from an AAV preparation comprising AAV vector particles and AAV empty capsids, to provide an AAV product substantially free of AAV empty capsids, said method comprising:
   (a) applying an AAV preparation comprising AAV vector particles and AAV empty capsids to a cation exchange chromatography column under conditions whereby said AAV vector particles and said AAV empty capsids bind the column;
   (b) adding a salt buffer to the column from (a) under conditions whereby AAV vector particles are eluted and AAV empty capsids remain bound to the column;
   (c) collecting eluted fractions from (b) that comprise AAV vector particles;
   (d) applying the AAV preparation from (c) to a second cation exchange chromatography column under conditions whereby said AAV vector particles and said AAV empty capsids bind the column;
   (e) adding a salt buffer to the column from (d) under conditions whereby AAV vector particles are eluted and AAV empty capsids remain bound to the column; and
   (f) collecting eluted fractions from (e) that comprise AAV vector particles to provide an AAV product substantially free of AAV empty capsids.

11. The method of claim 10, further comprising:
(g) applying the fractions from step (f) to an anion exchange chromatography column under conditions whereby said AAV vector particles and AAV empty capsids, if present, bind the column;
(h) adding a salt buffer to the column from (g) under conditions whereby AAV empty capsids are eluted and AAV vector particles remain bound to the column;
(i) adding a salt buffer with a greater salt concentration relative to the buffer added in (h) to the column from (h) under conditions whereby AAV vector particles are eluted; and
(j) collecting eluted fractions from (i) that comprise AAV vector particles to provide an AAV product substantially free of AAV empty capsids.

* * * * *